United States Patent [19]

Watanabe et al.

[11] Patent Number: 4,623,739
[45] Date of Patent: Nov. 18, 1986

[54] NITROGEN-CONTAINING ORGANOSILICON COMPOUNDS

[75] Inventors: Junichiro Watanabe; Yuichi Funahashi, both of Ohta, Japan

[73] Assignee: Toshiba Silicone Co., Ltd., Tokyo, Japan

[21] Appl. No.: 822,981

[22] Filed: Jan. 24, 1986

[30] Foreign Application Priority Data

Mar. 26, 1985 [JP] Japan ................................ 60-61261

[51] Int. Cl.$^4$ ............................................. C07F 7/10
[52] U.S. Cl. ................................... 556/410; 556/412
[58] Field of Search ............................... 556/410, 412

[56] References Cited

U.S. PATENT DOCUMENTS 2,762,823 9/1956 Speier ........................... 556/410 X Primary Examiner—Paul F. Shaver
Attorney, Agent, or Firm—Gary L. Loser

[57] ABSTRACT

A nitrogen-containing organosilicon compound represented by the general formula:

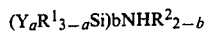

wherein $R^1$ stands for a saturated or unsaturated monovalent hydrocarbon group of 1 to 8 carbon atoms, $R^2$ for a saturated or unsaturated monovalent hydrocarbon group of 1 to 6 carbon atoms, Y for

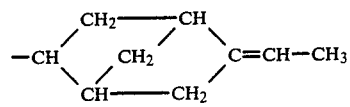

or

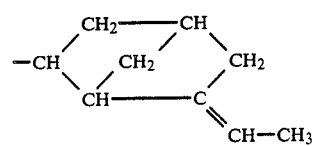

a for an integer of the value of 1 to 3, and b for an integer of the value of 1 to 2.

1 Claim, 3 Drawing Figures

NITROGEN-CONTAINING ORGANOSILICON COMPOUNDS

The present application claims priority of Japanese Patent Application Ser. No. 85/61261 filed on Mar. 26, 1985.

BACKGROUND OF THE INVENTION

This invention relates to novel and useful organosilicon compounds possessing an ethylidenenorbornyl group and containing a nitrogen atom, and more particularly to aminosilane and silazane compounds possessing an ethylidenenorbornyl group.

While various species of carbon functional aminosilanes and silazanes are used as silane coupling agents, aminosilanes and silazanes of the species which are in the form of a condensed ring and are possessed of an unsaturated group have never been known to the art.

SUMMARY OF THE INVENTION

The inventors have made a diligent study in search of aminosilane and silazane compounds which are in the form of a condensed ring and are possessed of an unsaturated group. They have consequently perfected this invention.

Specifically, this invention relates to a nitrogen-containing organosilicon compound represented by the general formula:

$$(Y_aR^1{}_{3-a}Si)_bNHR^2{}_{2-b}$$

wherein $R^1$ stands for a saturated or unsaturated monovalent hydrocarbon group of 1 to 8 carbon atoms, $R^2$ for a saturated or unsaturated monovalent hydrocarbon group of 1 to 6 carbon atoms, Y for

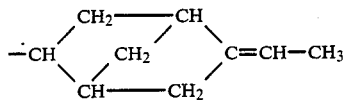

or

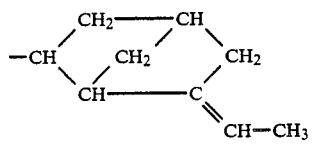

a for an integer of the value of 1 to 3, and b for an integer of the value of 1 to 2.

DESCRIPTION OF THE INVENTION

Figure 1:
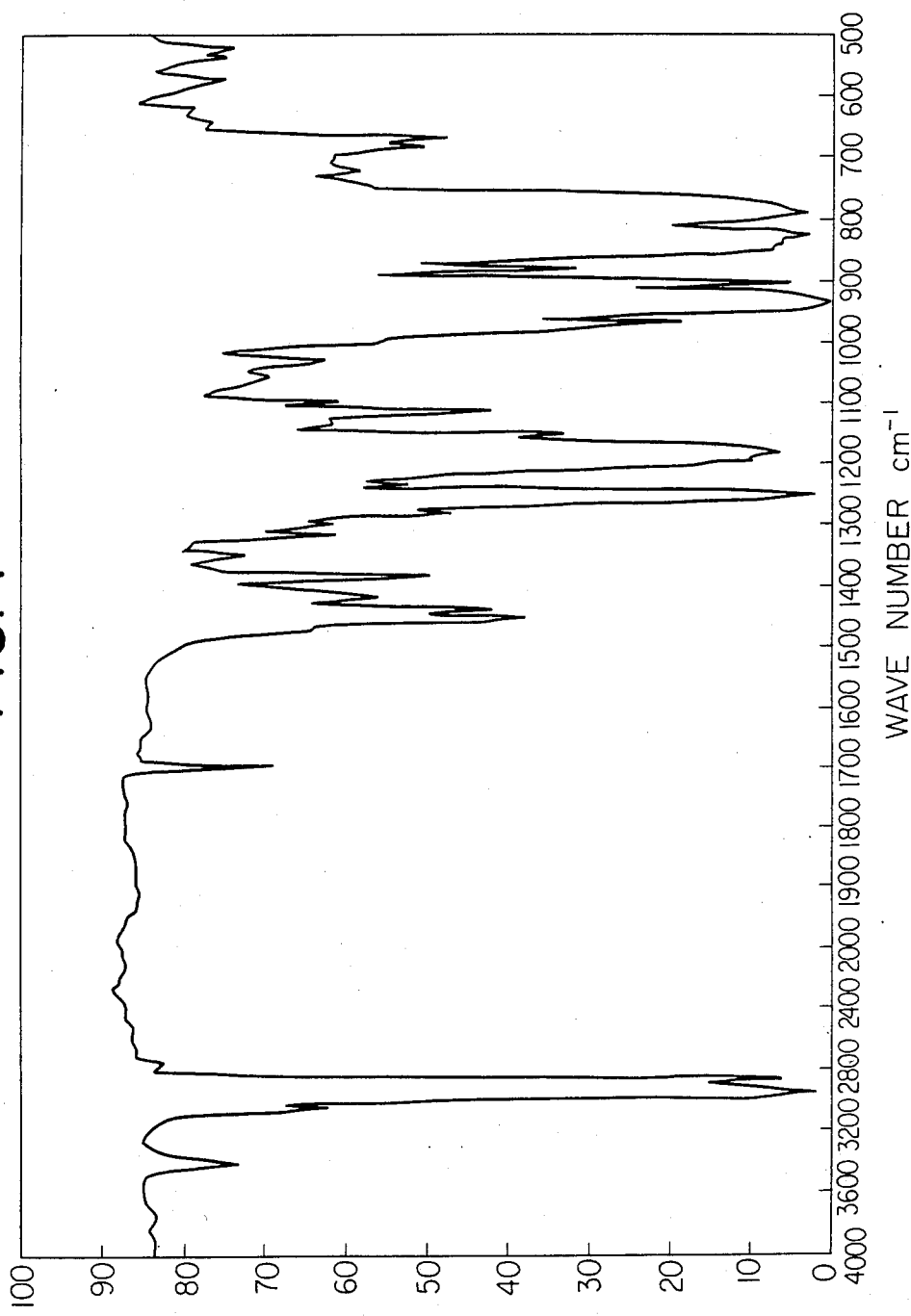
FIG. 1, FIG. 2, and FIG. 3 are infrared absorption spectra of the mixtures obtained respectively in Example 1, Example 2, and Example 3.

Illustrative of the saturated or unsaturated monovalent hydrocarbon group of 1 to 8 carbon atoms represented by $R^1$ in the general formula mentioned above, there may be cited alkyl groups such as methyl group, ethyl group, propyl group, and butyl group; alkenyl groups such as vinyl group and allyl group; aryl groups such as phenyl group and tolyl group; aralkyl groups such as benzyl group and β-phenylethyl group; and groups having a, cyano radical, halogen atom, or the like partially substituted for the hydrogen atoms bonded to the carbon atoms of the aforementioned monovalent hydrocarbon groups.

Illustrative of the saturated or unsaturated monovalent hydrocarbon group of 1 to 6 carbon atoms represented by $R^2$ in the same general formula, there may be cited alkyl groups such as methyl group, ethyl group, propyl group, butyl group, pentyl group, and hexyl group; phenyl group; cyclohexyl group, and groups having a cyano radical, a halogen atom, or the like partially substituted for the hydrogen atoms bonded to the carbon atoms of the monovalent hydrocarbon groups mentioned above.

Typical aminosilane and silazane compounds possessed of an ethylidenenorbornyl group according to this invention are cited below. It is provided that the symbol Y has the same meaning as defined above. For the sake of simplicity, the following symbols will be used: Me for methyl group, Et for ethyl group, Ph for phenyl group, Vi for vinyl group, and t-Bu for tert-butyl group.

$YMe_2SiNHSiMe_3$,
$[YMe_2Si]_2NH$,
$YMe_2SiNHSiMe_2Vi$,
$Y_2MeSiNHSiMe_3$,
$YMePhSiNHSiMe_3$,
$[YMePhSi]_2NH$,
$YMe_2SiNHMe$,
$YMe_2SiNHEt$,
$YMe_2SiNHt\text{-}Bu$ The methods (1) and (2) for production of the aforementioned silazane compounds possesed of an ethylidenenorbornyl group and the method (3) for production of aminosilane compounds possessed of an ethylidenenorbornyl group will be briefly described below.

(1) A chlorosilane containing an ethylidenenorbornyl group and ammonia are allowed to react with each other under ambient pressure or under application of pressure at 0° to 150° C., with continued elimination of the heat of reaction.

(2) A chlorosilane containing an ethylidenenorbornyl group, trioganochlorosilane containing no ethylidenenorbornyl group, and ammonia allowed to react with one another under ambient pressure or under application of pressure at 0° to 150° C., with continued elimination of the heat of reaction.

(3) A chlorosilane containing an ethylidenenorobornyl group and a primary amine are allowed to react with each other under ambient pressure or under application of pressure at 0° to 150° C., with continued elimination of the heat of reaction.

EXAMPLES OF THE INVENTION

Now, the present invention will be described with reference to working examples. Wherever "parts" are mentioned, they are meant as "parts by weight."

EXAMPLE 1

In a flask provided with a stirrer, a reflux condenser, and a thermometer, 100 parts of ethylidenenorbornyl dimethylchlorosilane and 200 parts of toluene were stirred. Through a glass tube dipped into the resultant solution in the flask, 12 parts of ammonia gas were supplied over a period of 15 hours. During the reaction which occured, the heat of reaction was removed so that the liquid temperature would remain at about 40° C. The reaction mixture so produced was left cooled and the cooled reaction mixture was filtered to remove by-product ammonium chloride. Then, the filtrate was heated at 100° C. under a vacuum (10 mmHg) to be stripped of toluene and raw materials. By distilling the residue, there was obtained 80 parts (92% in yield) of a 1:1.1 mixture of the compounds (a) and (b) represented by the following formulas:

[YMe$_2$Si]$_2$NH (a)

wherein Y = —CH(CH$_2$—CH$_2$)(CH—CH$_2$)C=CH—CH$_3$ and [YMe$_2$Si]$_2$NH (b)

wherein Y = —CH(CH$_2$—CH$_2$)(CH—C)CH$_2$
                                         ‖
                                         CH—CH$_3$

| | |
|---|---|
| Boiling point | 207° C./9 mmHg |
| Refractive index (n$_D^{25}$) | 1.513 |
| Specific gravity (25° C.) | 0.959 |
| Molecular weight | 373 |
| | (gas-mass spectral analysis) |

| | Elementary analysis | |
|---|---|---|
| | Found | Calculated (as C$_{22}$H$_{39}$NSi$_2$) |
| C | 70.5 | 70.8 |
| H | 10.6 | 10.4 |
| N | 3.5 | 3.8 |
| Si | 15.4 | 15.0 |
| Infrared absorption spectrum FIG. 1. | | |

EXAMPLE 2

In a flask provided with a stirrer, a reflux condenser, and a thermometer, 100 parts of ethylidenenorbornyl dimethyl chlorosilane, 50.6 parts of trimethylchlorosilane, and 300 parts of toluene were stirred. Then, through a glass tube dipped into the resultant solution in the flask, 24 parts of ammonia gas were supplied over a period of 20 hours. During the reaction which occurred, the heat of reaction was removed so that the liquid temperature would remain at about 40° C. The reaction mixture so produced was cooled and the cooled reaction mixture was filtered to remove by-product ammonium chloride. Then, the filtrate was heated 100° C. under a vacuum (10 mmHg) to be stripped of toluene and raw materials. By distilling the residue, there was obtained 52 parts (42% in yield) of a 1:1.1 mixture of the compounds (c) and (d) represented by the following formulas:

YMe$_2$SiNHSiMe$_3$ (c)

wherein Y = —CH(CH$_2$—CH$_2$)(CH—CH$_2$)C=CH—CH$_3$

YM$_2$SiNHSiMe$_3$ (d)

wherein Y = —CH(CH$_2$—CH$_2$)(CH—C)CH$_2$
                                         ‖
                                         CH—CH$_3$ Boiling point 143° C./18 mmHg YMe$_2$SiNHSiMe$_3$ (c)

wherein Y = —CH(CH$_2$—CH$_2$)(CH—CH$_2$)C=CH—CH$_3$

YM$_2$SiNHSiMe$_3$ (d)

wherein Y = —CH(CH$_2$—CH$_2$)(CH—C)CH$_2$
                                         ‖
                                         CH—CH$_3$

| | |
|---|---|
| Refractive index (n$_D^{25}$) | 1.480 |
| Specific gravity (25° C.) | 0.901 |
| Molecular weight | 267 |
| | (gas-mass spectral analysis) |

Figure 2:
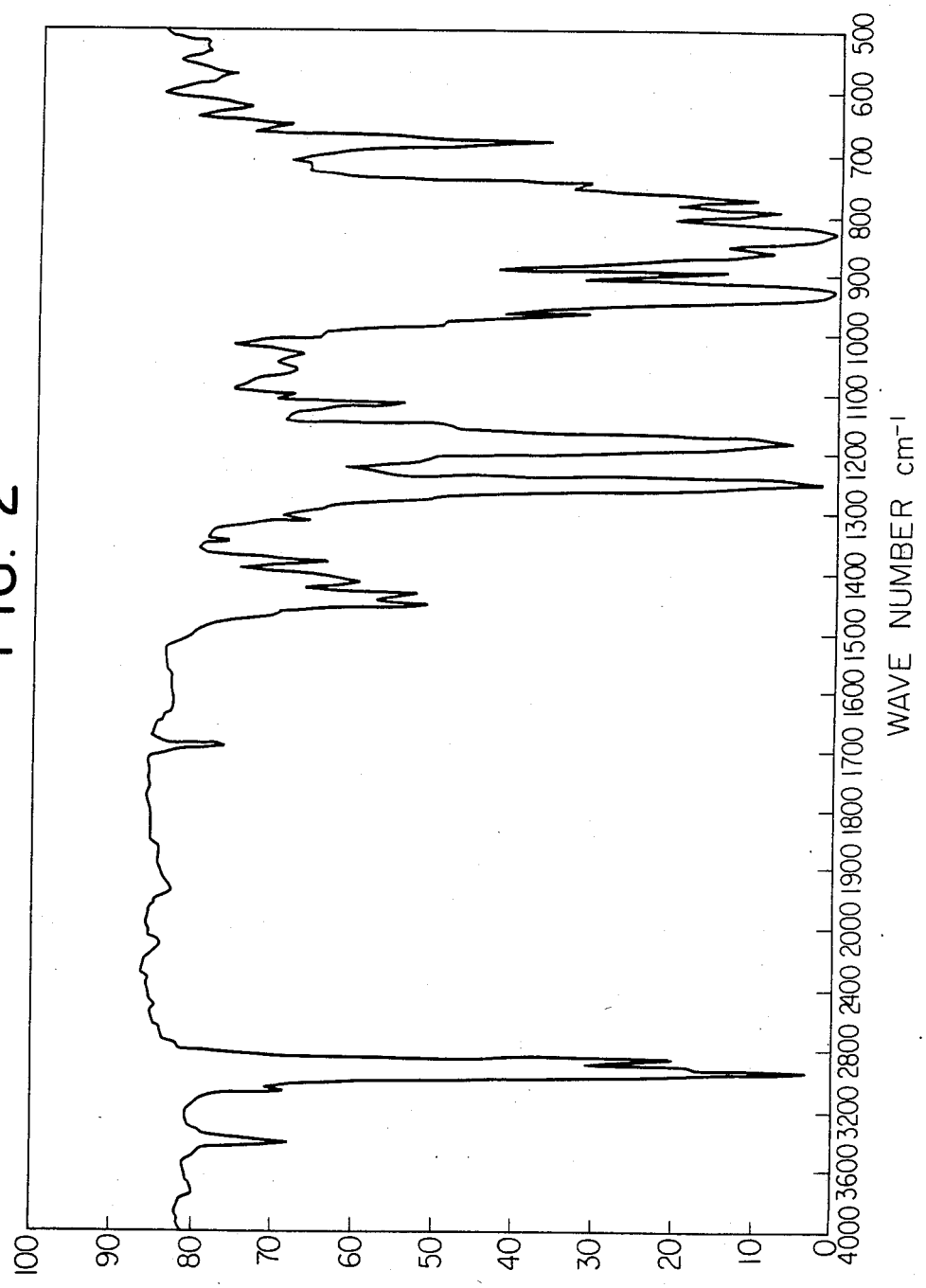

| | Elementary analysis | |
|---|---|---|
| | Found | Calculated (as C$_{14}$H$_{29}$NSi$_2$) |
| C | 60.3 | 62.9 |
| H | 10.8 | 10.9 |
| N | 5.3 | 5.2 |
| Si | 21.6 | 21.0 |
| Infrared absorption spectrum FIG. 2. | | |

EXAMPLE 3

In a flask provided with a stirrer, a reflux condenser, and a thermometer, 100 parts of ethylenenorbornyl dimethylchlorosilane, 56.2 parts of vinyldimethylchlorosilane, and 300 parts of toluene were stirred. Then, through a glass tube dipped into the resultant solution in the flask, 12 parts of ammonia gas were supplied over a period of 15 hours. During the reaction which occured, the heat of reaction was removed so that the liquid temperature would remain at about 40° C. The reaction mixture so produced was cooled and the cooled reaction mixture was filtered to remove by-product ammonium chloride. Then, the filtrate was heated at 100° C. under a vacuum (10 mmHg) to be stripped of toluene and raw materials. By distilling the residue, there was obtained 59 parts (45% in yield) of a 1:1.1 mixture of the compounds (e) and (f) represented by the following formulas:

YMe$_2$SiNHSiMe$_2$Vi (e)

wherein Y = —CH(CH$_2$—CH$_2$)(CH—CH$_2$)C=CH—CH$_3$

YMe$_2$SiNHSiMe$_2$Vi (f)

wherein Y = —CH(CH$_2$—CH$_2$)(CH—C)CH$_2$
                                         ‖
                                         CH—CH$_3$

| | |
|---|---|
| Boiling point | 129° C./7 mmHg |
| Refractive index (n$_D^{25}$) | 1.489 |
| Specific gravity (25° C.) | 0.914 |
| Molecular weight | 279 |
| | (gas-mass spectral analysis) |

| | Elementary analysis | |
|---|---|---|
| | Found | Calculated (as C$_{15}$H$_{29}$NSi$_2$) |
| C | 64.2 | 64.5 |
| H | 10.3 | 10.4 |

-continued

YMe₂SiNHSiMe₂Vi (e)

wherein Y = —CH(CH₂—CH₂—CH—CH₂—C=CH—CH₃ cyclic) (ethylidenenorbornyl group)

YMe₂SiNHSiMe₂Vi (f)

wherein Y = —CH(CH₂—CH₂—CH—CH₂—C(=CH—CH₃)—CH₂ cyclic)

|   |     |     |
|---|-----|-----|
| N | 5.5 | 5.0 |
| Si | 20.0 | 20.1 |

Figure 3:
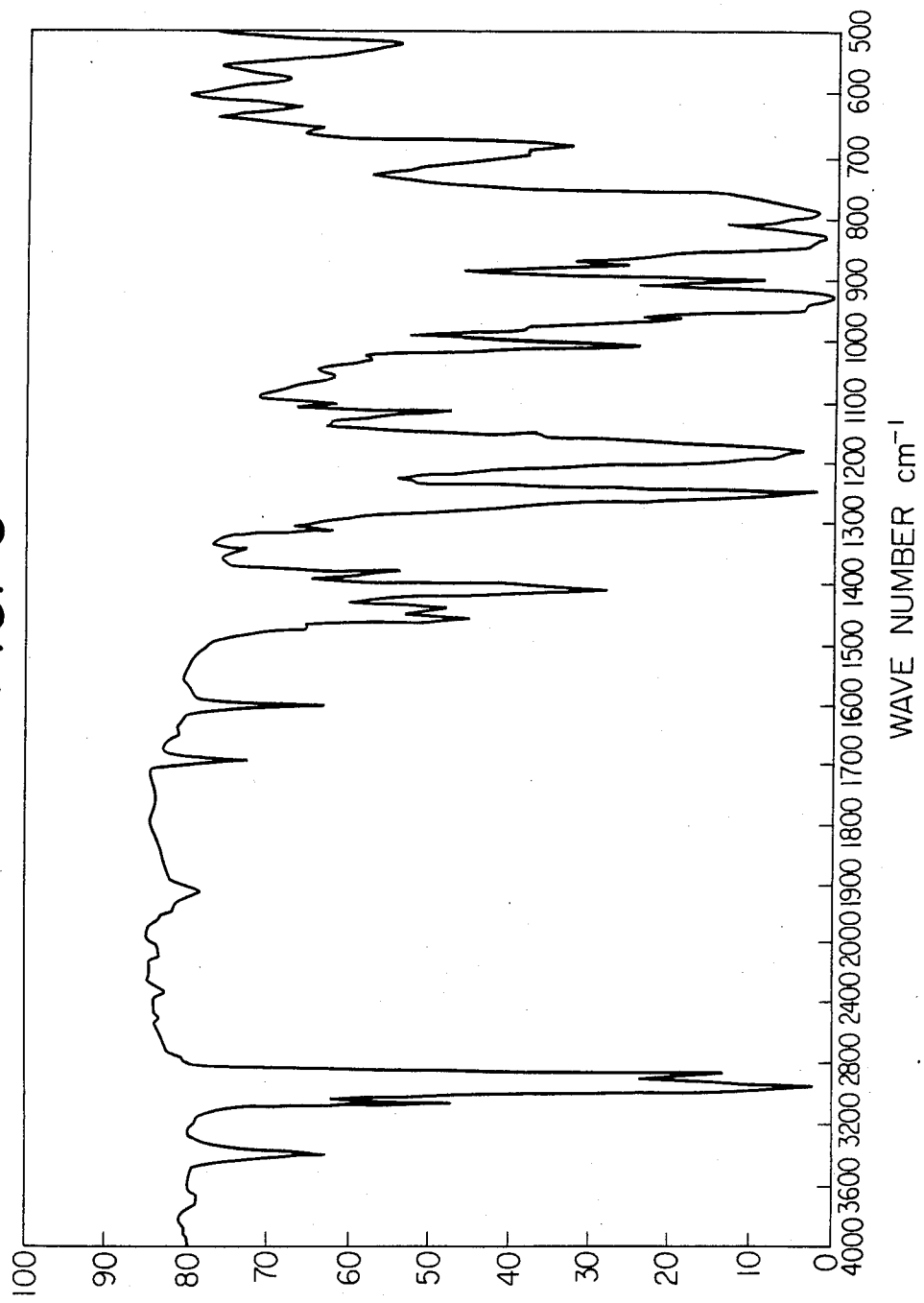

Infrared absorption spectrum FIG. 3

EXAMPLE 4

In a flask provided with a dropping funnel, a stirrer, a reflux condenser, and a thermometer, 100 parts of ethylidenenorbornyl dimethylchlorosilane and 400 parts of toluene were stirred. Through the dropping funnel, 68 parts of tert-butylamine were added dropwise to the resultant solution in the flask over a period of 10 hours. During the reaction which occured, the heat of reaction was removed so that the liquid temperature would remain at about 40° C. The reaction mixture so produced was cooled and the cooled reaction mixture was washed with cold water to separate off by-product tert-butylamine hydrochloride. Then, the upper layer liquid was heated at 100° C. under a vacuum (10 mmHg) to be stripped of toluene and raw materials. By distilling the residue, there was obtained 80 parts (68% yield) of a 1:1.1 mixture of the compounds (g) and (h) represented by the following formulas:

YMe₂SiNHt-Bu (g)

wherein Y = —CH(CH₂—CH₂—CH—CH₂—C=CH—CH₃ cyclic)

YMe₂SiNHt-Bu (h)

wherein Y = —CH(CH₂—CH₂—CH—CH₂—C(=CH—CH₃)—CH₂ cyclic)

| Boiling point | 120° C./10 mmHg |
|---|---|
| Refractive index ($n_D^{25}$) | 1.497 |
| Specific gravity (25° C.) | 0.904 |
| Molecular weight | 251 |
| | (gas-mass spectral analysis) |

| | Elementary analysis | |
|---|---|---|
| | Found | Calculated ($C_{15}H_{29}NSi$) |
| C | 71.5 | 71.7 |
| H | 11.2 | 11.5 |
| N | 5.9 | 5.6 |
| Si | 11.4 | 11.2 |

We claim:

1. A nitrogen-containing organosilicon compound represented by the general formula:

$$(Y_a R^1_{3-a} Si)_b NHR^2_{2-b}$$

wherein $R^1$ stands for a saturated or unsaturated monovalent hydrocarbon group of 1 to 8 carbon atoms, $R^2$ for a saturated or unsaturated monovalent hydrocarbon group of 1 to 6 carbon atoms, Y for —CH(CH₂—CH₂—CH—CH₂—C=CH—CH₃ cyclic)

or

—CH(CH₂—CH₂—CH—CH₂—C(=CH—CH₃)—CH₂ cyclic)

a for an integer of the value of 1 to 3, and b for an integer of the value of 1 or 2.

* * * * *